(12) United States Patent
Kim et al.

(10) Patent No.: US 10,406,110 B2
(45) Date of Patent: Sep. 10, 2019

(54) COMPOSITION FOR INHIBITING ANGIOGENESIS COMPRISING NANOPARTICLE-VITREOUS BODY-BASED PROTEIN COMPLEX AS ACTIVE INGREDIENT, AND USE THEREOF

(71) Applicants: SEOUL NATIONAL UNIVERSITY R & DB FOUNDATION, Seoul (KR); KOREA RESEARCH INSTITUTE OF STANDARDS AND SCIENCE, Daejeon (KR)

(72) Inventors: Jeong Hun Kim, Seoul (KR); Dong Hyun Jo, Seoul (KR); Tae Geol Lee, Daejeon (KR)

(73) Assignees: Seoul National University R & DB Foundation, Seoul (KR); Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 15/743,895

(22) PCT Filed: Jul. 12, 2016

(86) PCT No.: PCT/KR2016/007570
§ 371 (c)(1),
(2) Date: Jan. 11, 2018

(87) PCT Pub. No.: WO2017/010790
PCT Pub. Date: Jan. 19, 2017

(65) Prior Publication Data
US 2019/0015348 A1    Jan. 17, 2019

(30) Foreign Application Priority Data

Jul. 13, 2015 (KR) .................. 10-2015-0099308

(51) Int. Cl.
| | | |
|---|---|---|
| A61K 9/14 | (2006.01) | |
| A61K 9/51 | (2006.01) | |
| A61K 47/42 | (2017.01) | |
| A61P 27/02 | (2006.01) | |
| B82Y 5/00 | (2011.01) | |
| G01N 33/15 | (2006.01) | |
| G01N 33/68 | (2006.01) | |
| A61K 9/50 | (2006.01) | |
| A61K 9/16 | (2006.01) | |
| A61K 33/00 | (2006.01) | |
| A61K 33/24 | (2019.01) | |
| G01N 33/50 | (2006.01) | |
| A61K 47/69 | (2017.01) | |
| A61P 27/00 | (2006.01) | |
| A61K 9/00 | (2006.01) | |
| A61K 38/38 | (2006.01) | |
| B82Y 30/00 | (2011.01) | |

(52) U.S. Cl.
CPC .............. *A61K 9/51* (2013.01); *A61K 9/0048* (2013.01); *A61K 9/146* (2013.01); *A61K 9/16* (2013.01); *A61K 9/5052* (2013.01); *A61K 9/5169* (2013.01); *A61K 33/00* (2013.01); *A61K 33/24* (2013.01); *A61K 38/385* (2013.01); *A61K 47/42* (2013.01); *A61K 47/6923* (2017.08); *A61K 47/6925* (2017.08); *A61P 27/00* (2018.01); *A61P 27/02* (2018.01); *G01N 33/15* (2013.01); *G01N 33/50* (2013.01); *G01N 33/68* (2013.01); *B82Y 5/00* (2013.01); *B82Y 30/00* (2013.01)

(58) Field of Classification Search
CPC ........ A61K 9/146; A61K 9/16; A61K 9/1658; A61K 9/5052; A61K 9/51; A61K 9/5169; A61K 9/0048; A61K 33/00; A61K 33/242; A61K 38/1709; A61K 38/385; A61K 47/42; A61P 9/00; A61P 9/10; A61P 27/02; B82Y 5/00; B82Y 40/00; G01N 33/15; G01N 33/50; G01N 33/68
See application file for complete search history.

(56) References Cited

U.S. PATENT DOCUMENTS

2009/0110644 A1*  4/2009  Margel ............... A61K 41/0052
                                                    424/9.322
2017/0266318 A1*  9/2017  Belair .................. A61K 38/179

FOREIGN PATENT DOCUMENTS

KR    10-2014-0019641 A    2/2014

OTHER PUBLICATIONS

Arvizo et al. Mechanism of anti-angiogenic property of gold nanoparticles: role of nanoparticle size and surface charge. Nanomedicine: Nanotechnology, Biology, and Medicine. 2011, vol. 7, pp. 580-587. (Year: 2011).*

(Continued)

*Primary Examiner* — Jeffrey E. Russel
(74) *Attorney, Agent, or Firm* — Vorys, Sater, Seymour and Pease LLP; Mih Suhn Koh

(57) ABSTRACT

Provided is a nanoparticle-vitreous body-based protein complex, and more particularly, to a composition for inhibiting angiogenesis which includes the complex as an active ingredient, and a composition for preventing or treating an angiogenesis-related disease or a retinal disease. When the nanoparticle-vitreous body-based protein complex according to the subject matter is locally injected into the vitreous body, the complex exhibits significantly excellent binding strength with a vascular endothelial growth factor and thus can inhibit angiogenesis, thus being easily used to prepare a therapeutic agent for preventing, alleviating, or treating retinal and choroidal angiogenesis-related diseases.

10 Claims, 11 Drawing Sheets
Specification includes a Sequence Listing.

(56) References Cited

OTHER PUBLICATIONS

Chen et al. Surface properties, more than size, limiting convective distribution of virus-sized particles and viruses in the central nervous system. Journal of Neurosurgery. Aug. 2005, vol. 103, pp. 311-319. (Year: 2005).*
Schaffler et al. Blood protein coating of gold nanoparticles as potential tool for organ targeting. Biomaterials. Jan. 22, 2014, vol. 35, pp. 3455-3466. (Year: 2014).*
Hayashi et al., "Subretinal Delivery of Immunoglobulin G with Gold Nanoparticles in the Rabbit Eye" Japanese Journal of Ophthalmology, 2009, vol. 53, pp. 249-256.
Huo et al., "A Facile Nanoparticle Immunoassay for Cancer Biomarker Discovery" Journal of Nanobiotechnology, 2011, vol. 9:20, pp. 1-12.
Kemp et al., "Gold and silver nanoparticles conjugated with heparin derivative possess anti-angiogenesis properties" Nanotechnology, 2009, vol. 20, 455104, pp. 1-7.
Kim et al., "The inhibition of retinal neovascularization by gold nanoparticles via suppression of VEGFR-2 activation" Biomaterials, 2011, vol. 32, pp. 1865-1871.
Lee et al., "Characterization of Vascular Endothelial Growth Factor (VEGF) Receptors on the Endothelial Cell Surface During Hypoxia Using Whole Cell Binding Arrays" Analytical Biochemistry, 2007, vol. 369:2, pp. 241-247.
Saptarshi et al., "Interaction of nanoparticles with proteins: relation to bio-reactivity of the nanoparticle" Journal of Nanobiotechnology, 2013, vol. 11:26, pp. 1-12.

* cited by examiner

| Protein name | Accession | Average relative amount (%) |
|---|---|---|
| Vitrin | J9NXV3 | 12.46 |
| Secreted frizzled-related protein 2 | Q6GSH1 | 7.75 |
| Serum albumin | P49822 | 5.95 |
| Retinol-binding protein 3 | F1Q0V5 | 5.81 |
| Alpha-crystallin A chain | P02480 | 5.04 |
| Beta-crystallin S | A2BY7 | 2.66 |
| Complement C4-A | F1PWR2 | 2.31 |
| Alpha-enolase | F1PCH3 | 1.99 |
| Beta-crystallin B2 | Q2LEC2 | 1.87 |
| Retinal dehydrogenase 1 | E2RMX7 | 1.87 |
| Latent-transforming growth factor beta-binding protein 2 | J9P153 | 1.63 |
| Glyceraldehyde-3-phosphate dehydrogenase | Q28259 | 1.59 |
| Beta-crystallin B1 | E2R5F6 | 1.54 |
| Gelsolin | F6Y3P9 | 1.50 |
| EGF-containing fibulin-like extracellular matrix protein 1 | E2R612 | 1.46 |
| Opticin | P83286 | 1.43 |
| Spondin-1 | F6XC28 | 1.37 |
| Serotransferrin | J9P430 | 1.33 |
| Beta-crystallin A2 | J9NXL7 | 1.32 |
| Actin, cytoplasmic 2 | O18840 | 1.29 |

FIG. 2

| Protein name | Accession | Average relative amount (%) |
|---|---|---|
| Vitrin | J9NXV3 | 13.02 |
| Serum albumin | P49822 | 7.63 |
| Secreted frizzled-related protein 2 | Q863H1 | 7.43 |
| Retinol-binding protein 3 | F1Q0V5 | 5.48 |
| Alpha-crystallin A chain | P68280 | 4.20 |
| Beta-crystallin S | A2IBY7 | 2.93 |
| Beta-crystallin B2 | Q2LEC2 | 2.02 |
| Complement C4-A | F1PWR2 | 1.79 |
| Alpha-enolase | F1PCH3 | 1.78 |
| Retinal dehydrogenase 1 | E2RMX7 | 1.64 |
| Latent-transforming growth factor beta-binding protein 2 | J9P1S3 | 1.62 |
| Beta-crystallin B1 | E2R5F6 | 1.56 |
| Actin, cytoplasmic 1 | O18840 | 1.41 |
| Beta-crystallin A2 | J9NXL7 | 1.35 |
| Serotransferrin | J9P4J0 | 1.33 |
| Opticin | P83286 | 1.31 |
| Gelsolin | F6Y3P9 | 1.29 |
| Isoform 2 of Fibulin-2 | F1PRU3 | 1.22 |
| Spondin-1 | F6XC28 | 1.16 |
| Alpha B-crystallin protein | E2RNB6 | 1.14 |

FIG. 3

| Protein name | Accession | Average relative amount (%) |
|---|---|---|
| Vitrin | J9NXV3 | 10.54 |
| Secreted frizzled-related protein 2 | Q863H1 | 5.85 |
| Serum albumin | P49822 | 4.36 |
| Alpha-crystallin A chain | P68280 | 4.34 |
| Retinol-binding protein 3 | F1Q6V5 | 4.32 |
| Beta-crystallin S | A2IBY7 | 3.23 |
| Beta-crystallin B2 | Q2LEC2 | 2.87 |
| Complement C4-A | F1PWR2 | 2.33 |
| Latent-transforming growth factor beta-binding protein 2 | J9P1S3 | 2.30 |
| Spondin-1 | F6XC28 | 2.17 |
| Beta-crystallin B1 | E2RSF6 | 1.95 |
| Alpha-enolase | F1PCH3 | 1.79 |
| Beta-crystallin A2 | J9NXL7 | 1.73 |
| Gelsolin | F6Y3P9 | 1.59 |
| Ig gamma-1 chain C region | E2RCC8 | 1.49 |
| Retinol dehydrogenase 1 | E2RMX7 | 1.46 |
| Gamma-crystallin C | A3R1E2 | 1.44 |
| EGF-containing fibulin-like extracellular matrix protein 1 | E2R612 | 1.31 |
| Calsyntenin-1 | J9JHQ1 | 1.30 |
| Collagen alpha-1(II) chain | F1PS24 | 1.16 |

FIG. 4

| Protein name | Accession | Average relative amount (%) |
|---|---|---|
| Vitrin | J9NXV3 | 8.97 |
| Secreted frizzled-related protein 2 | Q863H1 | 6.15 |
| Serum albumin | P49822 | 3.82 |
| Retinol-binding protein 3 | F1Q0V5 | 3.80 |
| Calsyntenin-1 | J9JHQ1 | 3.77 |
| Alpha-crystallin A chain | P68280 | 3.34 |
| Collagen alpha-1(II) chain | F1PS24 | 2.78 |
| Latent-transforming growth factor beta-binding protein 2 | J9P1S3 | 2.56 |
| Alpha-enolase | F1PCH3 | 2.08 |
| Gelsolin | F6Y3P9 | 2.02 |
| Spondin-1 | F6XC28 | 1.91 |
| Complement C4-A | F1PWR3 | 1.65 |
| Beta-crystallin B1 | E2RSF6 | 1.62 |
| Beta-crystallin S | A2IBY7 | 1.62 |
| Complement factor B | E2RS80 | 1.61 |
| Retinal dehydrogenase 1 | E2RMX7 | 1.41 |
| Beta-crystallin B2 | Q1LEC2 | 1.39 |
| Pigment epithelium-derived factor | F2Z4Q7 | 1.30 |
| Actin, cytoplasmic 2 | O18840 | 1.26 |
| Isoform 2 of Fibulin-2 | F1PRU3 | 1.23 |

FIG. 5

| Protein name | Accession | Average relative amount (%) |
|---|---|---|
| Vitrin | J9NXV3 | 11.25 |
| Secreted frizzled-related protein 2 | Q863H1 | 6.80 |
| Serum albumin | P49822 | 5.44 |
| Retinol-binding protein 3 | F1Q0V5 | 4.85 |
| Alpha-crystallin A chain | P68280 | 4.23 |
| Beta-crystallin S | A1BY7 | 2.61 |
| Beta-crystallin B2 | Q2LEC2 | 2.04 |
| Latent-transforming growth factor beta-binding protein 2 | J9P153 | 2.02 |
| Complement C4-A | F1PWR2 | 2.02 |
| Alpha-enolase | F1PCH3 | 1.91 |
| Beta-crystallin B1 | E2R5F6 | 1.67 |
| Spondin-1 | F6XC28 | 1.65 |
| Catagranin-1 | J9JHQ1 | 1.64 |
| Gelsolin | F6Y3P9 | 1.60 |
| Retinal dehydrogenase 1 | E2RMX7 | 1.59 |
| Beta-crystallin A2 | J9NXL7 | 1.40 |
| Collagen alpha-1(II) chain | F1PS24 | 1.36 |
| Actin, cytoplasmic 1 | O18840 | 1.25 |
| EGF-containing fibulin-like extracellular matrix protein 1 | E2R612 | 1.22 |
| Opticin | P83286 | 1.21 |

FIG. 6

SEQUENCE LISTING

```
<160> NUMBER OF SEQ ID NOS: 5

<210> SEQ ID NO 1
<211> LENGTH: 678
<212> TYPE: PRT
<213> ORGANISM: Artificial Sequence
<220> FEATURE:
<223> OTHER INFORMATION: Vitrin

<400> SEQUENCE: 1

Met Arg Thr Val Val Leu Thr Met Lys Ala Ser Val Ile Glu Met Phe
1               5                   10                  15

Leu Val Leu Leu Val Thr Gly Val His Ser Asn Lys Glu Thr Ala Lys
            20                  25                  30

Lys Ile Lys Arg Pro Lys Phe Thr Val Pro Gln Ile Asn Cys Asp Val
        35                  40                  45

Lys Ala Gly Lys Ile Ile Asp Pro Glu Phe Ile Val Lys Cys Pro Ala
    50                  55                  60

Gly Cys Gln Asp Pro Lys Tyr His Val Tyr Gly Thr Asp Val Tyr Ala
65                  70                  75                  80

Ser Tyr Ser Ser Val Cys Gly Ala Ala Val His Ser Gly Val Leu Asp
```

```
                            85                    90                    95
Asn Ser Gly Gly Lys Ile Leu Val Arg Lys Val Ala Gly Gln Ser Gly
                100                   105                   110
Tyr Lys Gly Ser Tyr Ser Asn Gly Val Gln Ser Leu Ser Leu Pro Arg
                115                   120                   125
Trp Arg Glu Ser Phe Ile Val Leu Glu Ser Lys Pro Lys Lys Gly Val
            130                   135                   140
Thr Tyr Pro Ser Ala Leu Thr Tyr Ser Ser Lys Ser Pro Ala Ala
145                   150                   155                   160
Gln Ala Gly Glu Thr Thr Lys Ala Tyr Gln Arg Pro Pro Ile Pro Gly
                    165                   170                   175
Thr Thr Ala Gln Pro Val Thr Leu Met Gln Leu Leu Ala Val Thr Val
                180                   185                   190
Ala Val Ala Thr Pro Thr Thr Leu Pro Arg Pro Ser Pro Ser Ala Ala
                195                   200                   205
Ser Thr Thr Ser Ile Pro Arg Pro Gln Ser Val Gly His Arg Ser Gln
    210                   215                   220
Glu Met Asp Leu Trp Ser Thr Ala Thr Tyr Thr Ser Ser Gln Asn Arg
225                   230                   235                   240
Pro Arg Ala Asp Pro Gly Ile Gln Arg Gln Asp Pro Ser Gly Ala Ala
                    245                   250                   255
Phe Gln Lys Pro Val Gly Ala Asp Val Ser Leu Gly Leu Val Pro Lys
                260                   265                   270
Glu Glu Leu Ser Thr Gln Ser Leu Glu Pro Val Ser Leu Gly Asp Pro
                275                   280                   285
Asn Cys Lys Ile Asp Leu Ser Phe Leu Ile Asp Gly Ser Thr Ser Ile
            290                   295                   300
Gly Lys Arg Arg Phe Arg Ile Gln Lys Gln Leu Leu Ala Asp Val Ala
305                   310                   315                   320
Gln Ala Leu Asp Ile Gly Pro Ala Gly Pro Leu Met Gly Val Val Gln
                    325                   330                   335
Tyr Gly Asp Asn Pro Ala Thr His Phe Asn Leu Lys Thr His Thr Asn
                340                   345                   350
Ser Arg Asp Leu Lys Thr Ala Ile Glu Lys Ile Thr Gln Arg Gly Gly
            355                   360                   365
Leu Ser Asn Val Gly Arg Ala Ile Ser Phe Val Thr Lys Asn Phe Phe
    370                   375                   380
Ser Lys Ala Asn Gly Asn Arg Ser Gly Ala Pro Asn Val Val Val
385                   390                   395                   400
Met Val Asp Gly Trp Pro Thr Asp Lys Val Glu Glu Ala Ser Arg Leu
                    405                   410                   415
Ala Arg Glu Ser Gly Ile Asn Ile Phe Phe Ile Thr Ile Glu Gly Ala
                420                   425                   430
Ala Glu Asn Glu Lys Gln Tyr Val Val Glu Pro Asn Phe Ala Asn Lys
                435                   440                   445
Ala Val Cys Arg Thr Asn Gly Phe Tyr Ser Leu His Val Gln Ser Trp
    450                   455                   460
Phe Gly Leu His Lys Thr Leu Gln Pro Leu Val Lys Arg Val Cys Asp
465                   470                   475                   480
Thr Asp Arg Leu Ala Cys Ser Lys Thr Cys Leu Asn Ser Ala Asp Ile
                    485                   490                   495
Gly Phe Val Ile Asp Gly Ser Ser Ser Val Gly Thr Gly Asn Phe Arg
                500                   505                   510
```

```
Thr Val Leu Gln Phe Val Thr Asn Leu Thr Lys Glu Phe Glu Ile Ser
            515                 520                 525

Asp Thr Asp Thr Arg Ile Gly Ala Val Gln Tyr Thr Tyr Glu Gln Arg
        530                 535                 540

Leu Glu Phe Gly Phe Asp Lys Tyr Ser Ser Lys Pro Asp Ile Leu Asn
545                 550                 555                 560

Ala Ile Lys Arg Val Gly Tyr Trp Ser Gly Gly Thr Ser Thr Gly Ala
                565                 570                 575

Ala Ile Asn Phe Ala Leu Glu Gln Leu Phe Lys Lys Ser Lys Pro Asn
            580                 585                 590

Lys Arg Lys Leu Met Ile Leu Ile Thr Asp Gly Arg Ser Tyr Asp Asp
        595                 600                 605

Val Arg Ile Pro Ala Met Ala Ala His Leu Lys Gly Val Ile Thr Tyr
    610                 615                 620

Ala Ile Gly Val Ala Trp Ala Ala Gln Glu Glu Leu Glu Val Ile Ala
625                 630                 635                 640

Thr His Pro Ala Arg Asp His Ser Phe Phe Val Asp Glu Phe Asp Asn
                645                 650                 655

Leu His Gln Tyr Val Pro Arg Ile Ile Gln Asn Ile Cys Thr Glu Phe
            660                 665                 670

Asn Ser Gln Pro Arg Asn
            675

<210> SEQ ID NO 2
<211> LENGTH: 295
<212> TYPE: PRT
<213> ORGANISM: Artificial Sequence
<220> FEATURE:
<223> OTHER INFORMATION: Secreted frizzled-related protein 2

<400> SEQUENCE: 2

Met Leu Gln Gly Pro Gly Ser Leu Leu Leu Phe Leu Ala Ser His
1               5                   10                  15

Cys Cys Leu Gly Ser Ala Arg Gly Leu Phe Leu Phe Gly Gln Pro Asp
                20                  25                  30

Phe Ser Tyr Lys Arg Ser Asn Cys Lys Pro Ile Pro Ala Asn Leu Gln
            35                  40                  45

Leu Cys His Gly Ile Glu Tyr Gln Asn Met Arg Leu Pro Asn Leu Leu
        50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asp Asn Asp Ile Met Glu Thr Leu Cys Lys Asn
            180                 185                 190
```

```
Asp Phe Ala Leu Lys Ile Lys Val Lys Glu Ile Thr Tyr Ile Asn Arg
        195                 200                 205

Asp Thr Lys Ile Ile Leu Glu Thr Ser Lys Thr Ile Tyr Lys Leu
        210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Glu Leu Val Ile Thr Ser
                260                 265                 270

Val Lys Arg Trp Gln Lys Gly Gln Arg Glu Phe Lys Arg Ile Ser Arg
        275                 280                 285

Ser Ile Arg Lys Leu Gln Cys
        290                 295
```

<210> SEQ ID NO 3
<211> LENGTH: 609
<212> TYPE: PRT
<213> ORGANISM: Artificial Sequence
<220> FEATURE:
<223> OTHER INFORMATION: Albumin

<400> SEQUENCE: 3

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255
```

```
Lys Leu Val Thr Asp Leu Thr Lys Val His Thr Glu Cys Cys His Gly
            260                 265                 270

Asp Leu Leu Glu Cys Ala Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```

<210> SEQ ID NO 4
<211> LENGTH: 1247
<212> TYPE: PRT
<213> ORGANISM: Artificial Sequence
<220> FEATURE:
<223> OTHER INFORMATION: Retinol-binding protein 3

<400> SEQUENCE: 4

```
Met Met Arg Glu Trp Val Leu Leu Met Ser Val Leu Leu Cys Gly Leu
1               5                   10                  15

Ala Gly Pro Thr His Leu Phe Gln Pro Ser Leu Val Leu Asp Met Ala
            20                  25                  30

Lys Val Leu Leu Asp Asn Tyr Cys Phe Pro Glu Asn Leu Leu Gly Met
                35                  40                  45

Gln Glu Ala Ile Gln Gln Ala Ile Lys Ser His Glu Ile Leu Ser Ile
    50                  55                  60

Ser Asp Pro Gln Thr Leu Ala Ser Val Leu Thr Ala Gly Val Gln Ser
65                  70                  75                  80

Ser Leu Asn Asp Pro Arg Leu Val Ile Ser Tyr Glu Pro Ser Thr Pro
                85                  90                  95

Glu Pro Pro Pro Gln Val Pro Ala Leu Thr Ser Leu Ser Glu Glu Glu
            100                 105                 110

Leu Leu Ala Trp Leu Gln Arg Gly Leu Arg His Glu Val Leu Glu Gly
            115                 120                 125

Asn Val Gly Tyr Leu Arg Val Asp Ser Val Pro Gly Gln Glu Val Leu
    130                 135                 140

Ser Met Met Gly Glu Phe Leu Val Ala His Val Trp Gly Asn Leu Met
145                 150                 155                 160

Gly Thr Ser Ala Leu Val Leu Asp Leu Arg His Cys Thr Gly Gly Gln
                165                 170                 175

Val Ser Gly Ile Pro Tyr Ile Ile Ser Tyr Leu His Pro Gly Asn Thr
            180                 185                 190

Ile Leu His Val Asp Thr Ile Tyr Asn Arg Pro Ser Asn Thr Thr Thr
        195                 200                 205

Glu Ile Trp Thr Leu Pro Gln Val Leu Gly Glu Arg Tyr Gly Ala Asp
    210                 215                 220

Lys Asp Val Val Val Leu Thr Ser Ser Gln Thr Arg Gly Val Ala Glu
225                 230                 235                 240

Asp Ile Ala His Ile Leu Lys Gln Met Arg Arg Ala Ile Val Val Gly
                245                 250                 255

Glu Arg Thr Gly Gly Gly Ala Leu Asp Leu Arg Lys Leu Arg Ile Gly
            260                 265                 270

Glu Ser Asp Phe Phe Phe Thr Val Pro Val Ser Arg Ser Leu Gly Pro
    275                 280                 285

Leu Gly Gly Gly Ser Gln Thr Trp Glu Gly Ser Gly Val Leu Pro Cys
    290                 295                 300

Val Gly Thr Pro Ala Glu Gln Ala Leu Glu Lys Ala Leu Ala Ile Leu
305                 310                 315                 320

Thr Leu Arg Ser Ala Leu Pro Gly Val Val His Cys Leu Gln Glu Val
                325                 330                 335

Leu Lys Asp Tyr Tyr Thr Leu Val Asp Arg Val Pro Thr Leu Leu Gln
            340                 345                 350

His Leu Ala Ser Met Asp Phe Ser Thr Val Val Ser Glu Glu Asp Leu
    355                 360                 365

Val Thr Lys Leu Asn Ala Gly Leu Gln Ala Ala Ser Glu Asp Pro Arg
370                 375                 380

Leu Leu Val Arg Ala Ile Gly Pro Thr Glu Thr Pro Ser Trp Pro Ala
385                 390                 395                 400

Pro Asp Ala Ala Ala Glu Asp Ser Pro Gly Val Ala Pro Glu Leu Pro
            405                 410                 415

Glu Asp Glu Ala Ile Arg Gln Ala Leu Val Asp Ser Val Phe Gln Val
```

-continued

```
                420             425             430
Ser Val Leu Pro Gly Asn Val Gly Tyr Leu Arg Phe Asp Ser Phe Ala
            435             440             445
Asp Ala Ser Val Leu Gly Val Leu Ala Pro Tyr Val Leu Arg Gln Val
            450             455             460
Trp Glu Pro Leu Gln Asp Thr Glu His Leu Ile Met Asp Leu Arg His
465             470             475             480
Asn Pro Gly Gly Pro Ser Ser Ala Val Pro Leu Leu Ser Tyr Phe
            485             490             495
Gln Gly Pro Glu Ala Gly Pro Val His Leu Phe Thr Thr Tyr Asp Arg
            500             505             510
Arg Thr Asn Ile Thr Gln Glu His Phe Ser His Met Glu Leu Pro Gly
            515             520             525
Pro Arg Tyr Ser Thr Gln Arg Gly Val Tyr Leu Leu Thr Ser His Arg
            530             535             540
Thr Ala Thr Ala Ala Glu Glu Phe Ala Phe Leu Met Gln Ser Leu Gly
545             550             555             560
Trp Ala Thr Leu Val Gly Glu Ile Thr Ala Gly Asn Leu Leu His Thr
            565             570             575
Arg Thr Val Pro Leu Leu Asp Thr Pro Glu Gly Ser Leu Ala Leu Thr
            580             585             590
Val Pro Val Leu Thr Phe Ile Asp Asn His Gly Glu Ala Trp Leu Gly
            595             600             605
Gly Gly Val Val Pro Asp Ala Ile Val Leu Ala Glu Ala Leu Asp
            610             615             620
Lys Ala Gln Glu Val Leu Glu Phe His Gln Ser Leu Gly Ala Leu Val
625             630             635             640
Glu Gly Thr Gly His Leu Leu Glu Ala His Tyr Ala Arg Pro Glu Val
            645             650             655
Val Gly Gln Thr Ser Ala Leu Leu Arg Ala Lys Leu Ala Gln Gly Ala
            660             665             670
Tyr Arg Thr Ala Val Asp Leu Glu Ser Leu Ala Ser Gln Leu Thr Ala
            675             680             685
Asp Leu Gln Glu Val Ser Gly Asp His Arg Leu Leu Val Phe His Ser
            690             695             700
Pro Gly Glu Leu Val Val Glu Glu Ala Pro Pro Pro Pro Ala Val
705             710             715             720
Pro Ser Pro Glu Glu Leu Thr Tyr Leu Ile Glu Ala Leu Phe Lys Thr
            725             730             735
Glu Val Leu Pro Gly Gln Leu Gly Tyr Leu Arg Phe Asp Ala Met Ala
            740             745             750
Glu Leu Glu Thr Val Lys Ala Val Gly Pro Gln Leu Val Arg Leu Val
            755             760             765
Trp Gln Gln Leu Val Asp Thr Ala Ala Leu Val Ile Asp Leu Arg Tyr
            770             775             780
Asn Pro Gly Ser Tyr Ser Thr Ala Ile Pro Leu Leu Cys Ser Tyr Phe
785             790             795             800
Phe Glu Ala Glu Pro Arg Gln His Leu Tyr Ser Val Phe Asp Arg Ala
            805             810             815
Thr Ser Lys Val Thr Glu Val Trp Thr Leu Pro Gln Val Ala Gly Gln
            820             825             830
Arg Tyr Gly Ser His Lys Asp Leu Tyr Ile Leu Met Ser His Thr Ser
            835             840             845
```

Gly Ser Ala Ala Glu Ala Phe Ala His Thr Met Gln Asp Leu Gln Arg
    850                 855                 860

Ala Thr Val Ile Gly Glu Pro Thr Ala Gly Ala Leu Ser Val Gly
865                 870                 875                 880

Ile Tyr Gln Val Gly Ser Pro Leu Tyr Ala Ser Met Pro Thr Gln
            885                 890                 895

Met Ala Met Ser Ala Thr Thr Gly Lys Ala Trp Asp Leu Ala Gly Val
                900                 905                 910

Glu Pro Asp Ile Thr Val Pro Met Ser Glu Ala Leu Ser Ile Ala Gln
            915                 920                 925

Asp Ile Val Ala Leu Arg Ala Lys Val Pro Thr Val Leu Gln Thr Ala
            930                 935                 940

Gly Lys Leu Val Ala Asp Asn Tyr Ala Ser Ala Glu Leu Gly Ala Lys
945                 950                 955                 960

Met Ala Thr Lys Leu Ser Gly Leu Gln Ser Arg Tyr Ser Arg Val Thr
                965                 970                 975

Ser Glu Val Ala Leu Ala Glu Ile Leu Gly Ala Asp Leu Gln Met Leu
            980                 985                 990

Ser Gly Asp Pro His Leu Lys Ala Ala His Ile Pro Glu Asn Ala Lys
            995                 1000                1005

Asp Arg Ile Pro Gly Ile Val Pro Met Gln Ile Pro Ser Pro Glu Val
    1010                1015                1020

Phe Glu Glu Leu Ile Lys Phe Ser Phe His Thr Asn Val Leu Glu Asp
1025                1030                1035                1040

Asn Ile Gly Tyr Leu Arg Phe Asp Met Phe Gly Asp Gly Glu Leu Leu
                1045                1050                1055

Thr Gln Val Ser Arg Leu Leu Val Glu His Ile Trp Lys Lys Ile Met
                1060                1065                1070

His Thr Asp Ala Met Ile Ile Asp Met Arg Phe Asn Ile Gly Gly Pro
    1075                1080                1085

Thr Ser Ser Ile Pro Ile Leu Cys Ser Tyr Phe Phe Asp Glu Gly Pro
    1090                1095                1100

Pro Val Leu Leu Asp Lys Ile Tyr Ser Arg Pro Asp Asp Ser Val Ser
1105                1110                1115                1120

Glu Leu Trp Thr His Ala Gln Val Val Gly Glu Arg Tyr Gly Ser Lys
                1125                1130                1135

Lys Ser Met Val Ile Leu Thr Ser Ser Val Thr Ala Gly Thr Ala Glu
                1140                1145                1150

Glu Phe Thr Tyr Ile Met Lys Arg Leu Gly Arg Ala Leu Val Ile Gly
                1155                1160                1165

Glu Val Thr Ser Gly Gly Cys Gln Pro Pro Gln Thr Tyr His Val Asp
    1170                1175                1180

Asp Thr Asn Leu Tyr Leu Thr Ile Pro Thr Ala Arg Ser Val Gly Ala
1185                1190                1195                1200

Ser Asp Gly Ser Ser Trp Glu Gly Val Gly Val Thr Pro His Val Val
                1205                1210                1215

Val Pro Ala Glu Glu Ala Leu Ala Arg Ala Lys Glu Met Leu Gln His
            1220                1225                1230

Asn Gln Leu Arg Val Lys Arg Ser Pro Gly Leu Gln Asp His Leu
            1235                1240                1245

<210> SEQ ID NO 5
<211> LENGTH: 173

```
<212> TYPE: PRT
<213> ORGANISM: Artificial Sequence
<220> FEATURE:
<223> OTHER INFORMATION: Alpha-crystallin A chain

<400> SEQUENCE: 5

Met Asp Val Thr Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
            20                  25                  30

Glu Tyr Asp Leu Leu Pro Phe Leu Ser Ser Thr Ile Ser Pro Tyr Tyr
        35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Asp Asp Phe Val Glu Ile
            85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
            115                 120                 125

Leu Ser Cys Ser Leu Ser Ala Asp Gly Met Leu Thr Phe Cys Gly Pro
            130                 135                 140

Lys Ile Gln Thr Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170
```

COMPOSITION FOR INHIBITING ANGIOGENESIS COMPRISING NANOPARTICLE-VITREOUS BODY-BASED PROTEIN COMPLEX AS ACTIVE INGREDIENT, AND USE THEREOF

STATEMENT REGARDING GOVERNMENT RIGHTS

The present invention was undertaken with the support of 1) Innovative Nanobio-convergence Technology for Measurement and Control of Vascular Permeability in Diabetic Retinopathy No. 2012-0009544 grant funded by the National Research foundation of Korea, 2) Development of cell-based gene therapy for diabetic macular edema and dry age-related macular degeneration No. NRF-2015M3A9E6028949 grant funded by the National Research foundation of Korea.

SEQUENCE LISTING

The Sequence Listing submitted in text format (.txt) filed on Jun. 11, 2018, named "SequenceListing.txt", created on May 24, 2018 (24 KB), is incorporated herein by reference.

TECHNICAL FIELD

The present invention relates to a nanoparticle-vitreous body-based protein complex, and more particularly, to a composition for inhibiting angiogenesis which includes the complex as an active ingredient, and a composition for preventing or treating an angiogenesis-related disease or a retinal disease.

BACKGROUND ART

Angiogenesis is a biological process that provides tissues or organs with new blood vessels, and, in particular, refers to the growth of new capillaries from existing micro-vessels and is a fundamental process in which blood vessels are formed in the body after growth. The angiogenic process is very complicated and elaborate, and is briefly described as follows. First, when a stimulus for angiogenesis is transmitted to existing blood vessels, the blood vessels are expanded and membrane permeability thereof is increased. Second, fibrin is released to the outside of the expanded blood vessels to be deposited in a cytoplasmic matrix around the blood vessels. Third, enzymes for degrading a basement membrane of the existing blood vessels are activated, the basement membrane is destroyed, and endothelial cells are released from the blood vessels via the destroyed basement membrane and proliferate in the matrix of neighboring cells and migrate. Lastly, endothelial cells arranged in a row form blood vessels, thereby completing angiogenesis.

The angiogenic process is strictly regulated by various negative and positive regulators. When angiogenesis is abnormally regulated, various diseases such as cancer, rheumatoid arthritis, diabetic retinopathy, and the like occur. In particular, in a case in which this pathological angiogenesis occurs in the retina, the angiogenesis causes retinal edema, a retinal or vitreous hemorrhage, and retinal detachment. In addition, angiogenesis in the retina becomes a major cause of retinopathy of prematurity, diabetic retinopathy, and senile macular degeneration.

Meanwhile, nanoparticles (NPs) have been widely used for industrial and biomedical purposes. In particular, the NPs have been used as a promising material in biomedical fields such as drug delivery, gene delivery, intracellular imaging, and phototherapy, and, particularly, gold or silica nanomaterials have attracted much attention due to ease of synthesis and action, chemical stability, biocompatibility, and adjustable optical and electrical properties thereof.

Recently, gold or silver NPs have been known to inhibit vascular endothelial growth factor (VEGF)-induced angiogenesis, and studies on the development of angiogenesis inhibitors using the same have been conducted. However, to use the NPs in treatment, careful evaluation of the toxicity of NPs and efforts to minimize the toxicity are required.

DISCLOSURE

Technical Problem

The present invention has been made in view of the above problems, and as a result of having researched and made efforts to develop a nanoparticle therapeutic agent having a good effect on organ-specific inhibition of retinal and choroidal angiogenesis and exhibiting low toxicity, the inventors of the present invention verified that a nanoparticle-vitreous body-based protein complex exhibited remarkably excellent binding strength with a vascular endothelial growth factor, thus completing the present invention based on this finding.

Therefore, an object of the present invention is to provide a pharmaceutical composition for inhibiting angiogenesis, which includes a complex consisting of nanoparticles and a vitreous body-based protein surrounding surfaces of the nanoparticles, as an active ingredient.

In addition, another object of the present invention is to provide a composition for preventing or treating a retinal disease, which includes a complex consisting of nanoparticles and a vitreous body-based protein surrounding surfaces of the nanoparticles, as an active ingredient.

However, technical problems to be achieved by the present invention are not limited to the above-described technical problems, and other unmentioned technical problems will become apparent from the following description to those of ordinary skill in the art.

Technical Solution

The present invention provides a pharmaceutical composition for inhibiting angiogenesis, which includes a complex consisting of nanoparticles and a vitreous body-based protein surrounding surfaces of the nanoparticles, as an active ingredient.

In one embodiment of the present invention, the nanoparticles may be gold or silica.

In another embodiment of the present invention, the nanoparticles may have a diameter of 20 nm to 100 nm.

In another embodiment of the present invention, the angiogenesis may be involved in retinopathy of prematurity, proliferative retinopathy, age-related macular degeneration, diabetic macular edema (DME), diabetic retinopathy, or central serous (chorio)retinopathy.

In another embodiment of the present invention, the vitreous body-based protein may be one or more selected from the group consisting of vitrin, secreted frizzled-related protein 2, serum albumin, retinol-binding protein 3, and alpha-crystallin A chain.

The present invention provides a pharmaceutical composition for preventing or treating a retinal disease, which includes the composition as an active ingredient.

In one embodiment of the present invention, the retinal disease may be selected from the group consisting of retinopathy of prematurity, diabetic macular edema (DME), diabetic retinopathy, central serous (chorio)retinopathy, age-related macular degeneration, and proliferative retinopathy.

The present invention provides a method of screening a protein suitable for treating a retinal disease, the method including the following processes:

(1) injecting nanoparticles into a vitreous body in vitro;
(2) separating complexes of the nanoparticles and proteins in the vitreous body;
(3) binding the complexes to a vascular endothelial growth factor (VEGF); and
(4) selecting complexes bound to the VEGF.

The present invention provides a method of inhibiting angiogenesis, including administering a pharmaceutically effective amount of the pharmaceutical composition to an individual.

The present invention provides a method of preventing or treating a retinal disease, including administering a pharmaceutically effective amount of the pharmaceutical composition to an individual.

The present invention provides a use of the pharmaceutical composition for inhibiting angiogenesis.

The present invention provides a use of the pharmaceutical composition for preventing or treating a retinal disease.

Advantageous Effects

When a nanoparticle-vitreous body-based protein complex according to the present invention is locally injected into the vitreous cavity, the complex exhibits significantly excellent binding strength with a vascular endothelial growth factor, thus inhibiting angiogenesis, and, accordingly, can be easily used to prepare a therapeutic agent for preventing, alleviating, or treating retinal and choroidal angiogenesis-related diseases.

DESCRIPTION OF DRAWINGS

FIG. 2 illustrates the top 20 vitreous body-based proteins that formed a corona with gold nanoparticles having a diameter of 20 nm (Au20).

FIG. 3 illustrates the top 20 vitreous body-based proteins that formed a corona with silica nanoparticles having a diameter of 20 nm (Si20).

FIG. 4 illustrates the top 20 vitreous body-based proteins that formed a corona with gold nanoparticles having a diameter of 100 nm (Au100).

FIG. 5 illustrates the top 20 vitreous body-based proteins that formed a corona with silica nanoparticles having a diameter of 100 nm (Si100).

FIG. 6 illustrates the top 20 vitreous body-based proteins that formed a corona with nanoparticles as a combined result of FIGS. 2 to 5.

BEST MODE

Figure 1:
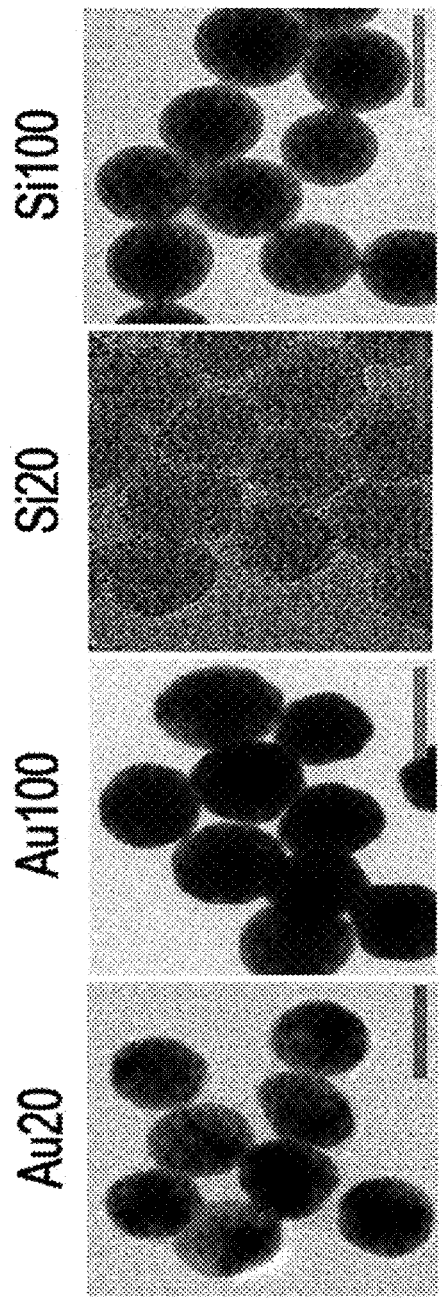
FIG. 1 illustrates transmission electron microscope (TEM) images of gold and silica nanoparticles having a diameter of 20 nm or 100 nm.

As a result of having researched and made efforts to develop a method capable of regulating retinal and choroidal angiogenesis, the inventors of the present invention verified that, when nanoparticles were locally injected into the vitreous cavity via a syringe, the nanoparticles formed a corona with vitreous body-based proteins, and such a nanoparticle-vitreous body-based protein complex exhibited significantly excellent binding strength with a vascular endothelial growth factor, thus completing the present invention based on this finding.

Hereinafter, the present invention will be described in detail.

The present invention provides a pharmaceutical composition for inhibiting angiogenesis, which includes a complex consisting of nanoparticles and a vitreous body-based protein surrounding surfaces of the nanoparticles, as an active ingredient.

The term "angiogenesis" as used herein refers to a process in which blood vessels are newly formed, i.e., the formation of new blood vessels in cells, tissues, or organs, and the term "new blood vessels" as used herein refers to blood vessels newly formed through angiogenesis. In the present invention, the terms "angiogenesis" and "new blood vessels" may be interchangeably described.

In addition, in the present invention, the angiogenesis may be involved in retinopathy of prematurity, proliferative retinopathy, age-related macular degeneration, diabetic macular edema (DME), diabetic retinopathy, central serous (chorio)retinopathy, or chronic inflammation, but the present invention is not limited thereto, and the angiogenesis may be involved in arbitrary diseases that occur or progress by angiogenesis.

The term "nanoparticles" as used herein refers to particles of various materials having a nano-sized diameter, and the nanoparticles are not particularly limited as long as they are nano-sized particles. However, when the diameter of the nanoparticles is greater than 100 nm or more, properties of nanoparticles may disappear, and thus the nanoparticles may have a diameter of 20 nm to 100 nm. In addition, the nanoparticles may be gold nanoparticles or silica nanoparticles, but the present invention is not limited thereto.

The term "vitreous body-based protein" as used herein refers to a protein in the vitreous body which is capable of forming a complex by binding to nanoparticles, and examples of the vitreous body-based protein include, but are not limited to, vitrin, secreted frizzled-related protein 2, serum albumin, retinol-binding protein 3, alpha-crystallin A chain, beta-crystallin S, beta-crystallin B2, latent-transforming growth factor beta-binding protein 2, complement C4-A, alpha-enolase, beta-crystallin B1, spondin-1, calsyntenin-1, gelsolin, retinal dehydrogenase 1, beta-crystallin A2, collagen alpha-1(II) chain, actin, cytoplasmic 1, EGF-containing fibulin-like extracellular matrix protein 1, and opticin. Preferably, the vitreous body-based protein may include one or more proteins selected from the group consisting of vitrin, secreted frizzled-related protein 2, serum albumin, retinol-binding protein 3, and alpha-crystallin A chain. Meanwhile, the vitrin, the secreted frizzled-related protein 2, the serum albumin, the retinol-binding protein 3, and the alpha-crystallin A chain may consist of amino acid sequences of SEQ ID NOS: 1 to 5, respectively, but the present invention is not limited thereto, and may include amino acid sequences with at least 70% homology, preferably, at least 80% homology, more preferably, at least 90%, and most preferably, at least 95% homology to the above-described respective amino acid sequences.

The nanoparticle-vitreous body-based protein complex included as an active ingredient in the composition according to the present invention exhibits excellent binding strength with a vascular endothelial growth factor, and thus may effectively inhibit angiogenesis.

According to one embodiment of the present invention, the top five vitreous body-based proteins, which bind to nanoparticles, were identified (see Example 1), the top five proteins and nanoparticles were incubated to form a nanoparticle-vitreous body-based protein complex (see Example 2), and then as a result of verifying an angiogenesis inhibition effect thereof, it was confirmed that binding strength of the complex to a vascular endothelial growth factor in water showed little difference as compared to the case of nanoparticles, whereas the complex exhibited significantly superior binding strength with a vascular endothelial growth factor in the vitreous body as compared to the case of a nanoparticle only-treated group (see Example 3).

In another embodiment of the present invention, as a result of verifying an angiogenesis inhibition effect of the nanoparticle-vitreous body-based protein complex in vitro or in vivo, it was confirmed that the nanoparticle-vitreous body-based protein complex exhibited an excellent angiogenesis inhibition effect both in vitro and in vivo (see Example 4).

From these experimental results, it can be seen that the nanoparticle-vitreous body-based protein complex according to the present invention inhibits angiogenesis, and thus may be effectively used for preventing, alleviating, or treating angiogenesis-related diseases, in particular, retinal and choroidal angiogenesis-related diseases.

Therefore, another embodiment of the present invention provides a pharmaceutical composition for preventing or treating an angiogenesis-related disease, which includes a complex consisting of nanoparticles and a vitreous body-based protein surrounding surfaces of the nanoparticles, as an active ingredient.

In addition, another embodiment of the present invention provides a pharmaceutical composition for preventing or treating a retinal disease, which includes a complex consisting of nanoparticles and a vitreous body-based protein surrounding surfaces of the nanoparticles, as an active ingredient.

The term "prevention" as used herein means all actions that inhibit angiogenesis-related diseases or retinal diseases or delay the onset thereof via administration of the pharmaceutical composition according to the present invention.

The term "treatment" as used herein means all actions that alleviate or beneficially change symptoms due to angiogenesis-related diseases or retinal diseases via administration of the pharmaceutical composition according to the present invention.

The term "angiogenesis-related diseases" as used herein refers to diseases occurring as a result of abnormal progression of the above-described angiogenesis, and examples thereof include, but are not limited to, retinopathy of prematurity, proliferative retinopathy, age-related macular degeneration, diabetic retinopathy, and central serous (chorio)retinopathy.

The term "retinal diseases" as used herein refers to diseases occurring such that a lesion occurs in the retina, and examples thereof include, but are not limited to, retinopathy of prematurity, diabetic macular edema (DME), diabetic retinopathy, central serous (chorio)retinopathy, age-related macular degeneration, and proliferative retinopathy.

The pharmaceutical composition according to the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including the type of diseases of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered consecutively or simultaneously with existing therapeutic agents, and may be administered in a single dose or multiple doses. It is important to administer the pharmaceutical composition in the minimum amount that enables achievement of the maximum effects without side effects in consideration of all the above-described factors, and this may be easily determined by those of ordinary skill in the art.

The pharmaceutical composition according to the present invention may be formulated into various oral or parenteral dosage forms when clinically administered, may be preferably applied by an intravitreal injection method, and may be prepared as pharmaceutical preparations suitable for injection into the vitreous cavity.

Another embodiment of the present invention provides a method of treating an angiogenesis-related disease or a retinal disease, which includes administering a complex consisting of nanoparticles and a vitreous body-based protein surrounding surfaces of the nanoparticles to an individual.

The term "individual" as used herein refers to a subject with diseases requiring a treatment and, more particularly, includes mammals such as humans or non-human primates, e.g., mice, rats, dogs, cats, horses, cows, and the like.

Another embodiment of the present invention provides a method of screening a protein suitable for treating a retinal disease, including the following processes:

(1) injecting nanoparticles into a vitreous body in vitro;
(2) separating complexes of the nanoparticles and proteins in the vitreous body;
(3) binding the complexes to a vascular endothelial growth factor (VEGF); and
(4) selecting complexes bound to the VEGF.

Hereinafter, exemplary embodiments will be described to aid in understanding of the present invention. However, the following examples are provided to more easily understand the present invention and are not intended to limit the scope of the present invention.

EXAMPLES

Example 1. Verification of Vitreous Body-Based Protein Binding to Nanoparticles 1-1. Preparation of Nanoparticles As nanoparticles for binding to vitreous body-based proteins, gold and silica nanoparticles having a diameter of 20 nm and gold and silica nanoparticles having a diameter of 100 nm were prepared. Specific information and TEM images of the nanoparticles are shown in Table 1 and FIG. 1.

TABLE 1

|  | Au20 | Au100 | Si20 | Si100 |
|---|---|---|---|---|
| Diameter (nm) | 18.99 ± 1.37 | 8.42 ± 7.24 | 20.72 ± 1.48 | 2.28 ± 4.78 |
| Hydrodynamic Diameter (nm) | 24.66 ± 0.83 | 112.16 ± 8.53 | 19.79 ± 0.70 | 130.04 ± 3.71 |
| Zeta potential (mV) | −45.26 ± 1.46 | −43.54 ± 0.41 | −52.96 ± 6.86 | −45.94 ± 3.62 |

1-2. Binding Between Nanoparticles and Vitreous Body-Based Protein

Each of the gold (Au20) and silica (Si20) nanoparticles ($1 \times 10^{11}$) having a diameter of 20 nm and the gold (Au100) and silica (Si100) nanoparticles ($1 \times 10^{11}$) having a diameter of 100 nm, prepared through Example 1-1, and the vitreous body containing 170 μg of proteins were incubated in a microcentrifuge tube at 4° C. for 6 hours while being rotated at 20 rpm. Subsequently, the resulting product was centrifuged at 15,000 rpm for 20 minutes to obtain a precipitate, and then washed twice with distilled water to remove non-specifically bound proteins. At this time, the precipitate includes free nanoparticles and protein-bound nanoparticles. The precipitate was suspended in 30 μL of Laemmli buffer, and heated at 100° C. for 3 minutes to induce separation of nanoparticles and proteins. Thereafter, the separated resultant was centrifuged at 15,000 rpm for 1 minute to obtain a supernatant, protein analysis was performed using the supernatant, and the top 20 vitreous body-based proteins that formed a corona with the respective nanoparticles were identified, and the results thereof are shown in FIGS. 2 to 5. In addition, the top 20 vitreous body-based proteins were identified by combining the above results all together, and the results thereof are shown in FIG. 6.

As illustrated in FIG. 6, it was confirmed that the top 5 vitreous body-based proteins, which form a corona with nanoparticles, were vitrin, secreted frizzled-related protein 2, serum albumin, retinol-binding protein 3, and alpha-crystallin A chain in this order, and relative amounts thereof were 11.25%, 6.80%, 5.44%, 4.85%, and 4.23%, respectively.

Example 2. Formation of Nanoparticle-Vitreous Body-Based Protein Complex

A total 150 ng of proteins (SALVAR complex) consisting of the top 5 vitreous body-based proteins that were identified by Example 1-2 having weights of 50 ng, 25 ng, 25 ng, 25 ng, and 25 ng, respectively was prepared, and the total 150 ng of proteins and $1 \times 10^9$ nanoparticles were incubated at 4° C. for 1 hour while being rotated at 20 rpm to form a nanoparticle-vitreous body-based protein complex.

Example 3. Verification of Angiogenesis Inhibition Effect of Nanoparticle-Vitreous Body-Based Protein Complex Gold and silica nanoparticles are known to bind to a vascular endothelial growth factor in water or in a cell culture. Thus, to verify whether the nanoparticle-vitreous body-based protein complex according to the present invention effectively binds to a vascular endothelial growth factor in water or in a cell culture as compared to such nanoparticles, an experiment was conducted as follows.

Figure 7A:
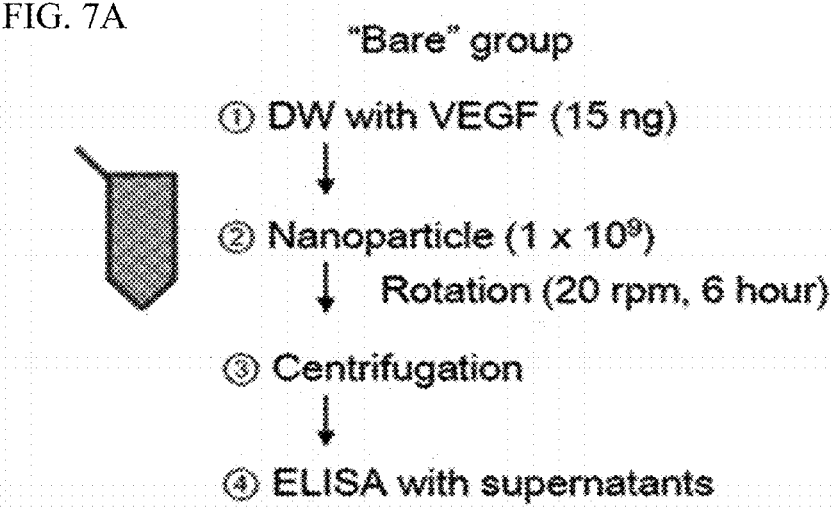
FIGS. 7A and 7B illustrate schematic processes of an experiment for comparing binding strengths of nanoparticles and a nanoparticle-vitreous body-based protein complex with respect to a vascular endothelial growth factor in water.
Figure 7B:
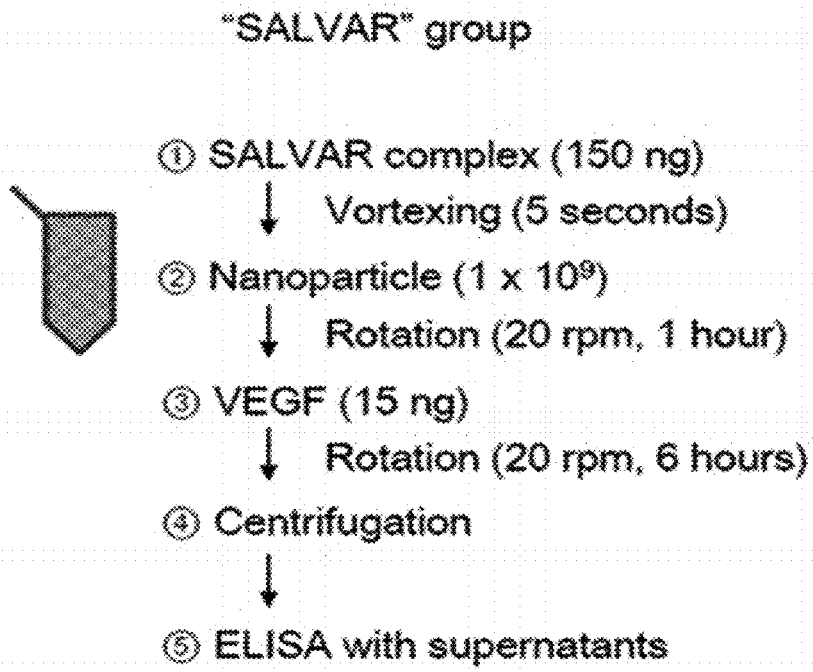

3-1. Comparison Between Binding Strengths with Vascular Endothelial Growth Factor in Water The case of binding nanoparticles to a vascular endothelial growth factor in water was compared with the case of binding the nanoparticle-vitreous body-based protein complex to a vascular endothelial growth factor in water, and schematic processes for the corresponding experiment are illustrated in FIGS. 7A and 7B.

That is, nanoparticles or the nanoparticle-vitreous body-based protein complex and a vascular endothelial growth factor were incubated at 4° C. for 6 hours while being rotated at 20 rpm. After incubation, the resultant product was centrifuged at 15,000 rpm for 20 minutes to precipitate a vascular endothelial growth factor bound to the nanoparticles or the nanoparticle-vitreous body-based protein complex, and a free vascular endothelial growth factor in the supernatant was measured by enzyme-linked immunosorbent assay to determine binding strengths with the vascular endothelial growth factor.

Figure 9:
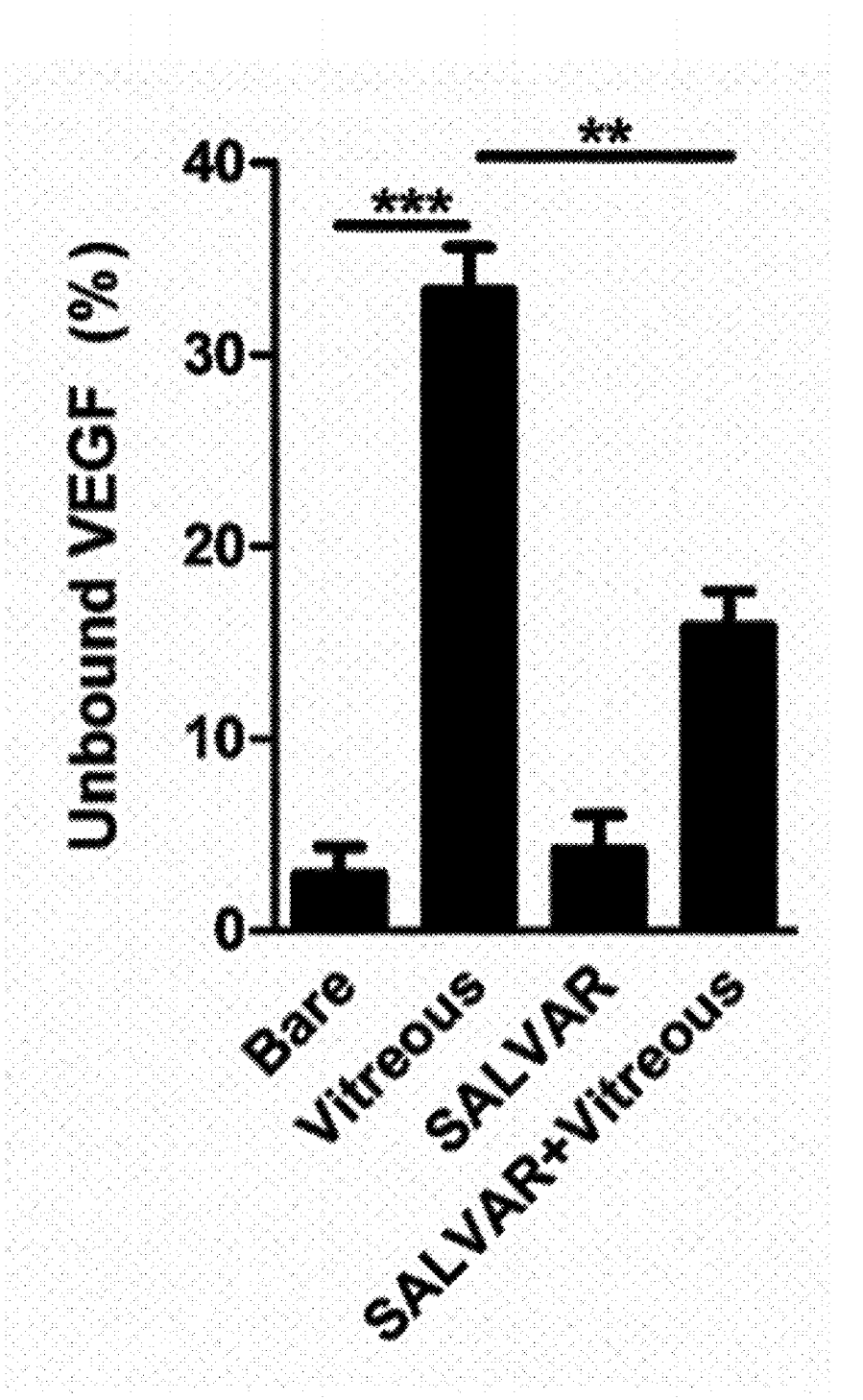
FIG. 9 is a graph showing results of comparing binding strengths of nanoparticles and a nanoparticle-vitreous body-based protein complex with respect to a vascular endothelial growth factor in water and in the vitreous body.

As a result, as illustrated in FIG. 9, it was confirmed that binding strengths with the vascular endothelial growth factor between the case of binding nanoparticles to a vascular endothelial growth factor in water ("Bare" group) and the case of binding the nanoparticle-vitreous body-based protein complex to a vascular endothelial growth factor ("SALVAR" group) showed little difference.

Figure 8A:
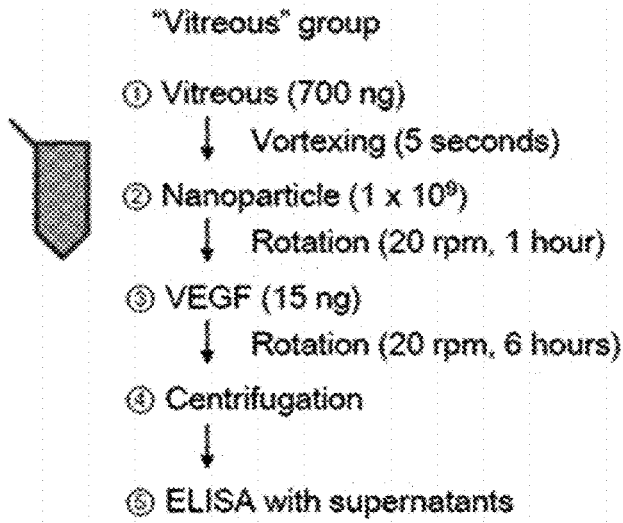
FIGS. 8A and 8B illustrate schematic processes of an experiment for comparing binding strengths of nanoparticles and a nanoparticle-vitreous body-based protein complex with respect to a vascular endothelial growth factor in the vitreous body.
Figure 8B:
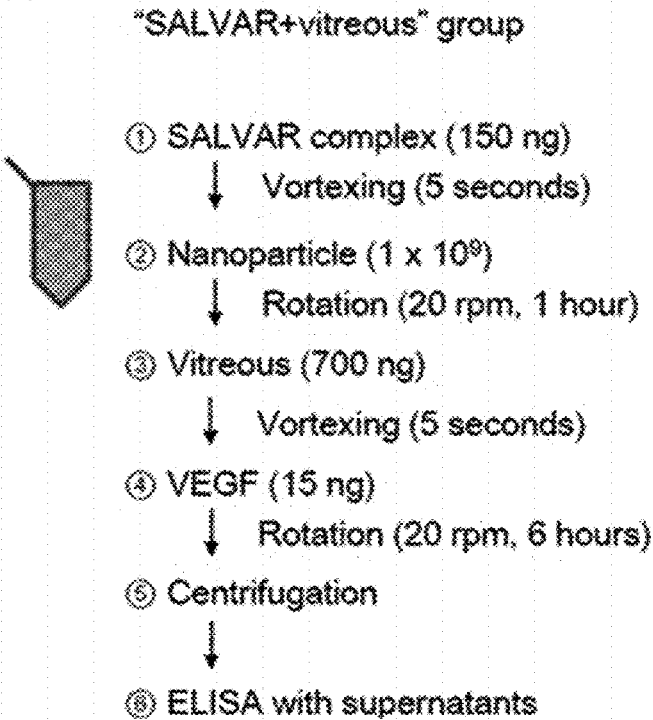

3-2. Comparison Between Binding Strengths with Vascular Endothelial Growth Factor In Vitreous Body The case of binding nanoparticles to a vascular endothelial growth factor in the vitreous body was compared with the case of binding the nanoparticle-vitreous body-based protein complex to the vascular endothelial growth factor in the vitreous body, and schematic processes for the corresponding experiment are illustrated in FIGS. 8A and 8B.

The experiment was conducted using the same method as that used in Example 3-1, except that the vitreous body was used instead of water.

As a result, as illustrated in FIG. 9, it was confirmed that the case of binding the nanoparticle-vitreous body-based protein complex to the vascular endothelial growth factor in the vitreous body ("SALVAR+Vitreous" group) exhibited significantly superior binding strength with the vascular endothelial growth factor as compared to the case of binding nanoparticles to the vascular endothelial growth factor in the vitreous body ("Vitreous" group).

From the above results, it can be seen that the nanoparticle-vitreous body-based protein complex according to the present invention exhibits an excellent therapeutic effect in vivo.

Example 4. Verification of In Vivo Angiogenesis Inhibition Effect of Nanoparticle-Vitreous Body-Based Protein Complex In Vitro It is known that, when vascular endothelial cells are treated with 20 ng/mL of a vascular endothelial growth factor, proliferation or tube formation of the vascular endothelial cells, which represents an angiogenic process, is accelerated. To verify whether administration of the nanoparticle-vitreous body-based protein complex inhibits an in vitro angiogenic process in which a vascular endothelial growth factor is involved, a test for proliferation and tube formation of vascular endothelial cells was conducted. The vascular endothelial cell proliferation test was carried out such that 2,000 vascular endothelial cells were cultured in each of a plurality of wells of a 0.3% gelatin-coated plate for 1 day, and then treated with a vascular endothelial growth factor, nanoparticles, a nanoparticle-vitreous body-based protein complex, and bevacizumab according to conditions, and degrees of proliferation of the vascular endothelial cells for 48 hours were compared with one another. The degrees of proliferation of the vascular endothelial cells were estimated using a method of directly measuring the number of the cells after trypan blue staining and a method of measuring 450 nm absorbance after water-soluble tetrazolium salt-1 treatment. The tube formation test was carried out such that 100,000 vascular endothelial cells in each of a plurality of wells of a Matrigel-coated plate were treated with a vascular endothelial growth factor, nanoparticles, a nanoparticle-vitreous body-based protein complex, and bevacizumab according to conditions, and degrees of tube formation of the vascular endothelial cells were compared with one another after 12 hours. Quantitative comparison was conducted by checking the number of formed tubes on a 50× magnification screen.

Figure 10A:
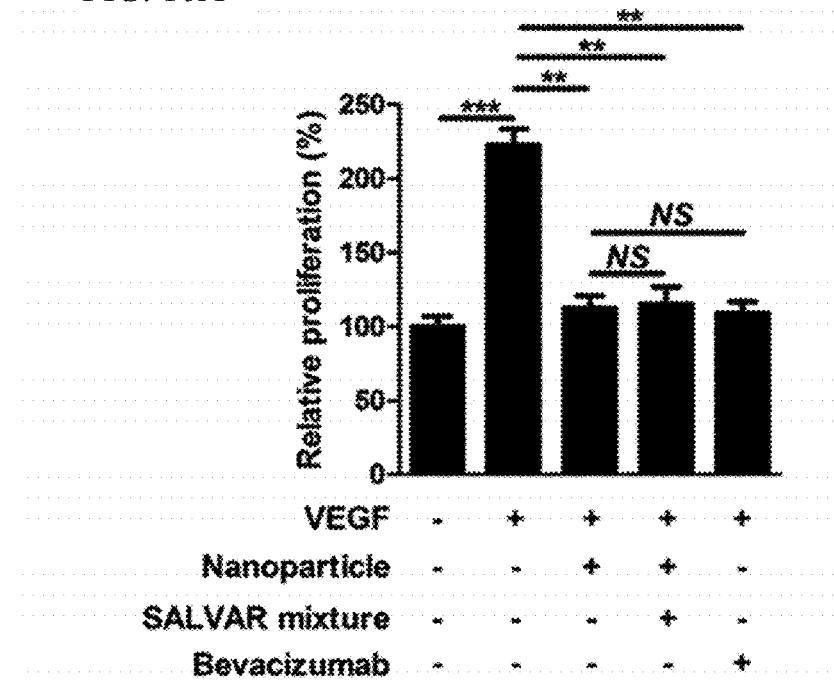
FIGS. 10A and 10B illustrate verification results of an in vivo angiogenesis inhibition effect of a nanoparticle-vitreous body-based protein complex in vitro.
Figure 10B:
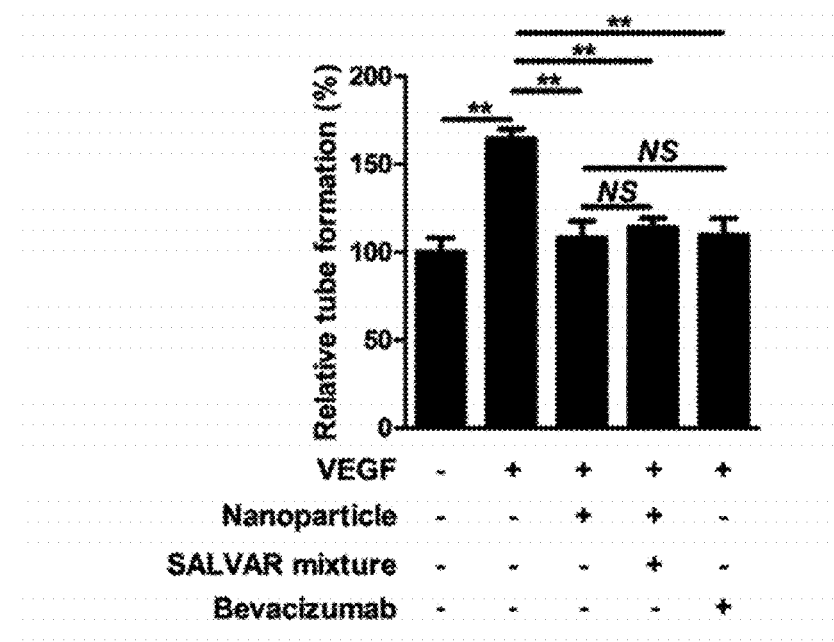

As a result, as illustrated in FIGS. 10A and 10B, it was confirmed that a case, in which the nanoparticle-vitreous body-based protein complex ("SALVAR mixture") was administered, exhibited an excellent angiogenesis inhibition effect equivalent to that of bevacizumab in the in vitro vascular endothelial cell proliferation and tube formation test.

Example 5. Verification of Angiogenesis Inhibition Effect of Nanoparticle-Vitreous Body-Based Protein Complex In Vivo A laser-induced choroidal neovascularization model was produced in mice, and nanoparticles or a nanoparticle-vitreous body-based protein complex was injected into the vitreous body to determine effects thereof. The retinae of the mice were irradiated with a diode laser at an intensity of 400 mW for a duration of 50 ms to cause destruction of the Bruch membrane between the retinal and choroidal layers. After laser irradiation, each of nanoparticles ($10^9$/mL, 1 μL), a nanoparticle-vitreous body-based protein complex ($10^9$/mL, 1 μL), and an anti-vascular endothelial growth factor antibody (1 μg) was injected into the vitreous body, degrees of choroidal neovascularization on day 7 after laser irradiation were verified through immunofluorescent staining.

Figure 11A:
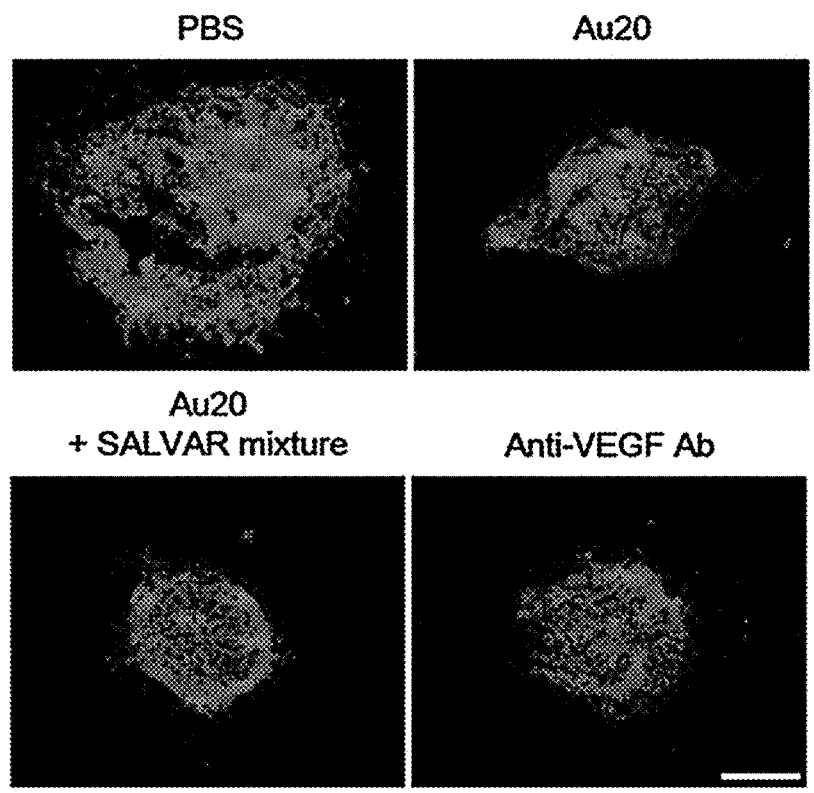
FIGS. 11A and 11B illustrate verification results of an angiogenesis inhibition effect of a nanoparticle-vitreous body-based protein complex in vivo.
Figure 11B:
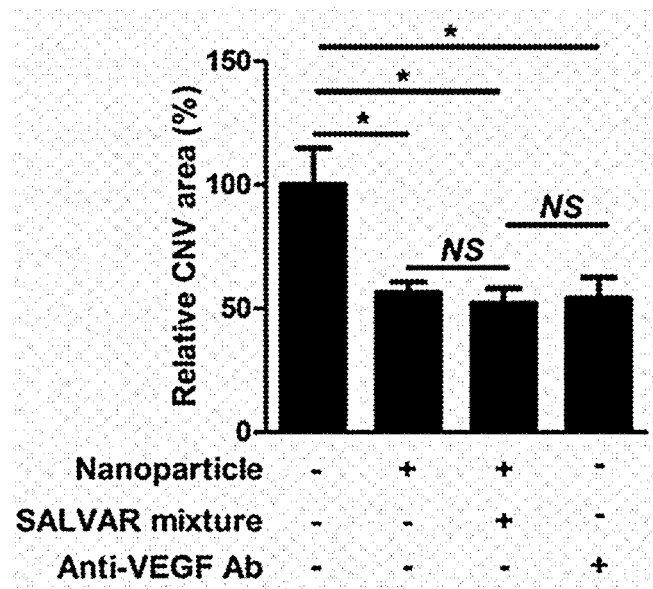

As a result, as illustrated in FIGS. 11A and 11B, it was confirmed that a case, in which the nanoparticle-vitreous body-based protein complex ("Au20+SALVAR mixture") was administered, exhibited an excellent angiogenesis inhibition effect equivalent to that of the anti-vascular endothelial growth factor antibody even in vivo.

The foregoing description of the present invention is provided for illustrative purposes only, and it will be understood by those of ordinary skill in the art to which the present invention pertains that the present invention may be easily modified in other particular forms without changing the technical spirit or essential characteristics of the present invention. Thus, the embodiments described herein should be construed as being provided for illustrative purposes only and not for purposes of limitation.

INDUSTRIAL APPLICABILITY

When a nanoparticle-vitreous body-based protein complex according to the present invention is locally injected into the vitreous body, the complex exhibits significantly excellent binding strength with a vascular endothelial growth factor and thus can inhibit angiogenesis, and thus can be used in pharmaceutical industrial fields related to retinal and choroidal angiogenesis-related diseases.

The invention claimed is:

1. A method of screening a protein suitable for treating a retinal disease, the method comprising the following processes:
   (1) injecting nanoparticles into a vitreous body in vitro;
   (2) separating complexes of the nanoparticles and proteins in the vitreous body;
   (3) binding the complexes to a vascular endothelial growth factor (VEGF); and
   (4) selecting complexes bound to the VEGF.

2. A method of inhibiting angiogenesis, including administering a pharmaceutically effective amount of a pharmaceutical composition to an individual, wherein the pharmaceutical composition comprises a complex consisting of nanoparticles and a vitreous body-based protein surrounding surfaces of the nanoparticles, as an active ingredient, wherein the nanoparticles are gold or silica.

3. The method of inhibiting angiogenesis of claim 2, wherein the nanoparticles have a diameter of 20 nm to 100 nm.

4. The method of inhibiting angiogenesis of claim 2, wherein the angiogenesis is involved in retinopathy of prematurity, diabetic macular edema (DME), diabetic retinopathy, central serous (chorio)retinopathy, age-related macular degeneration, or proliferative retinopathy.

5. The method of inhibiting angiogenesis of claim 2, wherein the vitreous body-based protein comprises one or more selected from the group consisting of vitrin, secreted frizzled-related protein 2, serum albumin, retinol-binding protein 3, and alpha-crystallin A chain.

6. The method of treating a retinal disease, including administering a pharmaceutically effective amount of a pharmaceutical composition to an individual, wherein the pharmaceutical composition comprises a complex consisting of nanoparticles and a vitreous body-based protein surrounding surfaces of the nanoparticles, as an active ingredient.

7. The method of treating a retinal disease of claim 6, wherein the nanoparticles are gold or silica.

8. The method of treating a retinal disease of claim 6, wherein the nanoparticles have a diameter of 20 nm to 100 nm.

9. The method of treating a retinal disease of claim 6, wherein the retinal disease is selected from the group consisting of retinopathy of prematurity, diabetic macular edema (DME), diabetic retinopathy, central serous (chorio) retinopathy, age-related macular degeneration, and proliferative retinopathy.

10. The method of treating a retinal disease of claim 6, wherein the vitreous body-based protein comprises one or more selected from the group consisting of vitrin, secreted frizzled-related protein 2, serum albumin, retinol-binding protein 3, and alpha-crystallin A chain.

* * * * *